(12) United States Patent
O'Hare

(10) Patent No.: US 10,222,492 B2
(45) Date of Patent: Mar. 5, 2019

(54) THREE-DIMENSIONAL COMPUTED TOMOGRAPHY GAUGE

(71) Applicant: Hexagon Metrology, Inc., North Kingstown, RI (US)

(72) Inventor: Jonathan J. O'Hare, East Greenwich, RI (US)

(73) Assignee: Hexagon Metrology, Inc., North Kingstown, RI (US)

(*) Notice: Subject to any disclaimer, the term of this patent is extended or adjusted under 35 U.S.C. 154(b) by 154 days.

(21) Appl. No.: 15/299,774

(22) Filed: Oct. 21, 2016

(65) Prior Publication Data

US 2017/0112462 A1    Apr. 27, 2017

Related U.S. Application Data

(60) Provisional application No. 62/245,409, filed on Oct. 23, 2015.

(51) Int. Cl.
*A61B 6/00* (2006.01)
*G01T 7/00* (2006.01)
(Continued)

(52) U.S. Cl.
CPC .............. *G01T 7/005* (2013.01); *A61B 6/032* (2013.01); *G01B 15/00* (2013.01); *G01N 23/046* (2013.01)

(58) Field of Classification Search
CPC ..................................................... A61B 6/583
See application file for complete search history.

(56) References Cited

U.S. PATENT DOCUMENTS 5,963,612 A    10/1999  Navab
6,364,529 B1   4/2002   Dawson
(Continued)

FOREIGN PATENT DOCUMENTS

DE  102006028452        12/2007
EP    1 760 457 A2       3/2007  ............. G01N 23/04
(Continued)

OTHER PUBLICATIONS

International Searching Authority, International Search Report—International Application No. PCT/US2017/034263, dated Jul. 14, 2017 together with the Written Opinion of the International Searching Authority, 10 pages.
(Continued)

*Primary Examiner* — Hoon K Song
(74) *Attorney, Agent, or Firm* — Nutter McClennen & Fish LLP

(57) ABSTRACT

A method of calibrating an x-ray computed tomography machine provides an x-ray computed tomography machine having calibration settings, and uses the x-ray computed tomography machine to produce a gauge reconstruction. The gauge has a first base supporting two or more objects, and a second base supporting two or more objects. The first base and the second base form a perpendicular configuration, and each of the plurality of objects is secured on at least one of the first base and the second base. Each of the objects has a center, and the distance between the centers of each object is known. The method then measures the distance between at least two objects to produce measured center distance values, compares the measured center distance values against the known center distance values, and uses the comparison to determine if there is a distance error in the gauge reconstruction.

28 Claims, 7 Drawing Sheets

(51) Int. Cl.
*A61B 6/03* (2006.01)
*G01B 15/00* (2006.01)
*G01N 23/046* (2018.01)

(56) References Cited

U.S. PATENT DOCUMENTS

| | | | |
|---|---|---|---|
| 7,738,624 | B2 | 6/2010 | Herold et al. |
| 8,911,149 | B2 | 12/2014 | O'Hare et al. |
| 2005/0094771 | A1 | 5/2005 | Basu et al. |
| 2005/0154548 | A1 | 7/2005 | Basel et al. |
| 2007/0122020 | A1 | 5/2007 | Claus et al. ............ 382/131 |
| 2008/0075227 | A1 | 3/2008 | Christoph et al. |
| 2008/0273654 | A1* | 11/2008 | Rappoport ............ A61B 6/037 378/18 |
| 2013/0195239 | A1* | 8/2013 | O'Hare ............ G01T 7/005 378/4 |
| 2014/0153694 | A1 | 6/2014 | Suppes et al. |

FOREIGN PATENT DOCUMENTS

| | | |
|---|---|---|
| WO | WO 2012/150336 A1 | 11/2012 |
| WO | WO 2014/122218 | 8/2014 |
| WO | WO 2015/199790 | 12/2015 |
| WO | WO 2017/070442 | 4/2017 |

OTHER PUBLICATIONS

Kruth et al., "Computed tomography for dimensional metrology," CIRP Annals—Manufacturing Technology, vol. 60, pp. 821-842, 2011.

Neugebauer et al., A Geometrical Standard for Testing of X-Ray Computer Tomography, Technisches Messen, vol. 74, No. 11, pp. 565-571, 2007.

International Searching Authority, International Search Report—International Application No. PCT/US2016/058067, dated Jan. 12, 2017, together with the Written Opinion of the International Searching Authority, 13 pages.

Lettenbauer et al., "Verification of the Accuracy of Computed Tomography, Systems for measuring 3-D technology," Quality Digest, https://www.qualitydigest.com/inside/twitter-ed/verification-accuracy-computed-tomography.html, 5 pages, Nov. 17, 2009.

\* cited by examiner

US 10,222,492 B2

THREE-DIMENSIONAL COMPUTED TOMOGRAPHY GAUGE

PRIORITY

This patent application claims priority from provisional U.S. provisional patent application No. 62/245,409, filed Oct. 23, 2015, entitled, "THREE-DIMENSIONAL COMPUTED TOMOGRAPHY GAUGE," and naming Jonathan J. O'Hare as inventor, the disclosure of which is incorporated herein, in its entirety, by reference.

FIELD OF THE INVENTION

The invention generally relates to computed tomography systems ("CT systems") and, more particularly, the invention relates to calibrating and/or verification of x-ray computed tomography devices/CT machines used to measure objects.

BACKGROUND OF THE INVENTION

Coordinate measuring machines (CMMs) are the gold standard for accurately measuring a wide variety of different types of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Inaccurate measurements can have catastrophic effects. Accordingly, to ensure that CMMs deliver accurate measurements, the CMM industry has developed well-defined accuracy verification standards, procedures, and gauging tools to calibrate and verify the underlying machines taking these measurements. To those ends, a CMM verification procedure typically requires hard gauges that are traceable for uncertainty calculations, and designed in such a way to ensure that they (i.e., the gauges) are dimensionally stable.

SUMMARY OF VARIOUS EMBODIMENTS

In accordance with one embodiment of the invention, a method of calibrating or verifying the dimensional accuracy of an x-ray computed tomography machine controls the x-ray computed tomography machine to produce a gauge reconstruction (a 3D reconstruction of the gauge). The gauge has a first base supporting two or more objects, and a second base supporting two or more objects. The first base and the second base form a perpendicular configuration, and each of the plurality of objects is secured on at least one of the first base and the second base. Each of the objects has a center, and the distance between the centers of each object is known ("known center distance values"). The method then measures, in the reconstructed three-dimensional volume or three-dimensional derived surface of the gauge ("gauge reconstruction"), the distance between at least two objects to produce measured center distance values, compares the measured center distance values against the known center distance values, and uses the comparison to determine if there is a distance error (i.e., the gauge is incorrectly measuring distances—e.g., out of specification) in the gauge reconstruction.

Among other things, the gauge reconstruction may include a point cloud. To reduce interference with the x-rays, at least one of the first base and the second base may have at least one hole through solid base material. Moreover, the second base may contact the first base along an edge of the first base. To ensure uniformity, each of the objects may substantially spherically shaped and identically sized and include a similar material (e.g., ruby).

In some embodiments, at least one of the objects contacts both the first base and the second base to at least in part form a straight line with other objects. For example, where first, second, and third objects of the plurality of objects form a substantially straight line, the method may measure between the first and second objects, and measuring between the first and third objects. A fourth object of the plurality of objects also may be part of the substantially straight line. In that case, the method may measure between the fourth object and at least one of the first, second and third objects. One of the noted first, second, third, or fourth objects may contact the two bases.

The method also may produce a plurality of 3D gauge reconstructions of the gauge from a plurality of x-ray projection images in different orientations. Then, the method may measure center distance values of the objects in each of the 3D gauge reconstructions against the respective known center distance values for calibrating the computed tomography machine. In this or other cases, if the method also determines that there is no distance error, then it may responsively maintain the calibration settings in the x-ray computed tomography machine. Conversely, if the method determines there is a distance error, it responsively may modify the calibration settings of the x-ray computed tomography machine. Those calibration settings are modified as a function of at least one of the differences.

The objects may include a given type of object, and the first base and the second base each may support at least two of the given type of object. Moreover, the first and second bases are formed from a base material, and the plurality of objects are formed from an object material. To enhance contrast under x-rays, the object material may have a higher attenuation to x-rays than that of the base material.

The x-ray computed topography machine may scan around the gauge in a number of manners. For example, it may scan around the gauge about an axis of rotation that diverges with either a) the first plane, b) the second plane, or c) both the first plane and the second plane.

Illustrative embodiments of the invention are implemented as a computer program product having a computer usable medium with computer readable program code thereon. The computer readable code may be read and utilized by a computer system in accordance with conventional processes.

In accordance with another embodiment, a gauge for calibrating or verifying the dimensional accuracy of an x-ray computed tomography machine has a plurality of objects formed from a material that is visible to x-rays. The plurality of objects are configured to receive x-rays without changing shape, and each one has both substantially the same shape and an object attenuation value to x-rays. The gauge also has a substantially planar first base fixedly supporting a first set of the plurality of objects, and a substantially planar second base fixedly supporting a second set of the plurality objects. The first base is connected to the second base to form a substantially right angle with the second base. The first and second sets of objects have a common object—i.e., at least one object is fixedly supported by both bases. The first base and second base have respective first and second base attenuation values. For appropriate contrast to x-rays, the object attenuation value is greater than the first and second base attenuation values.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an apparatus for calibrating (or verifying) an x-ray computed tomography machine enables more accurate measurements of a work piece—particularly, more accurate measurements of smaller dimensions of a work piece (e.g., in the sub-millimeter level, such as to the micrometer or nanometer level).

To that end, the apparatus has a first base that holds a plurality of objects in place. The apparatus also has a second base that holds a plurality of objects in place. The first base and the second base are positioned substantially perpendicular/orthogonal to one another. The perpendicular configuration of the first base and the second base positions objects on orthogonal planes, which allows measurement calibration and verification at steep and orthogonal angles. This arrangement further enables independent characterization of vertical and horizontal errors. Details are discussed below.

Figure 1A:
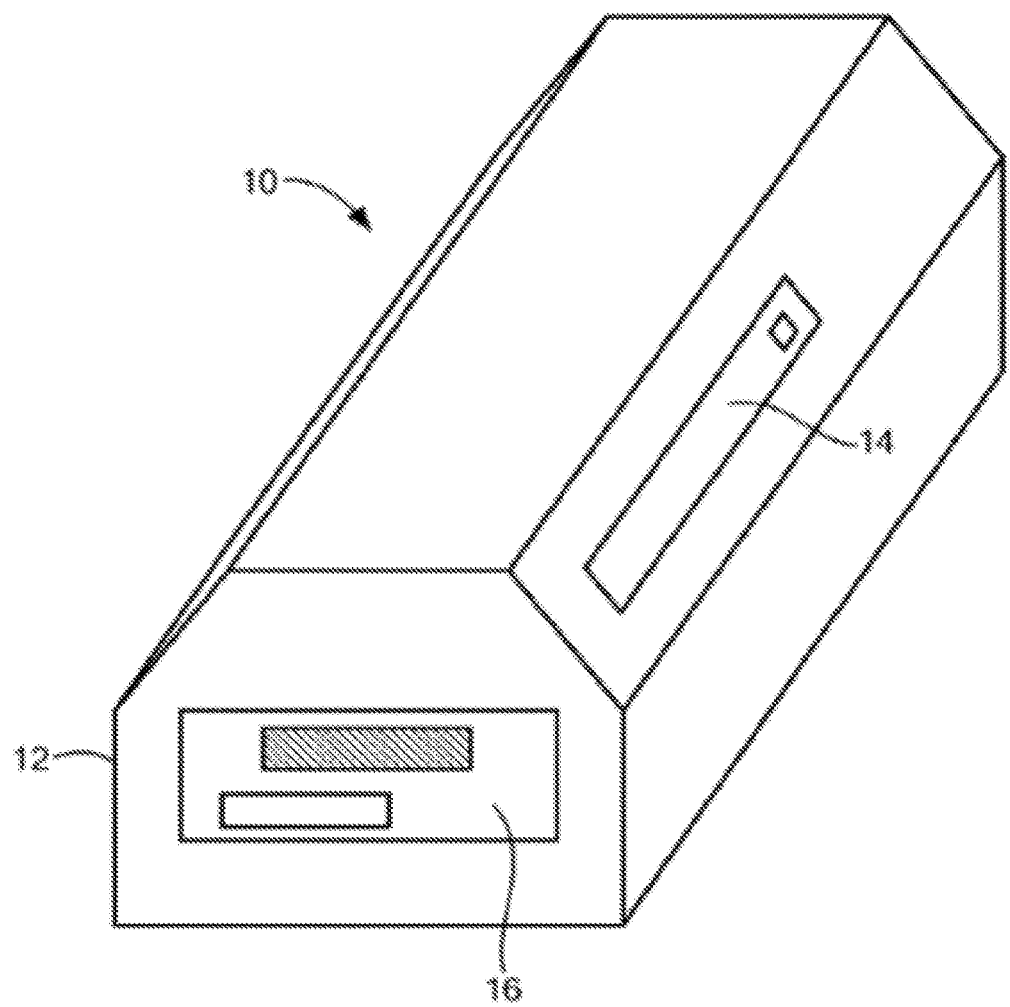
FIG. 1A schematically shows an x-ray computed tomography device that may use illustrative embodiments of the invention.
Figure 1B:
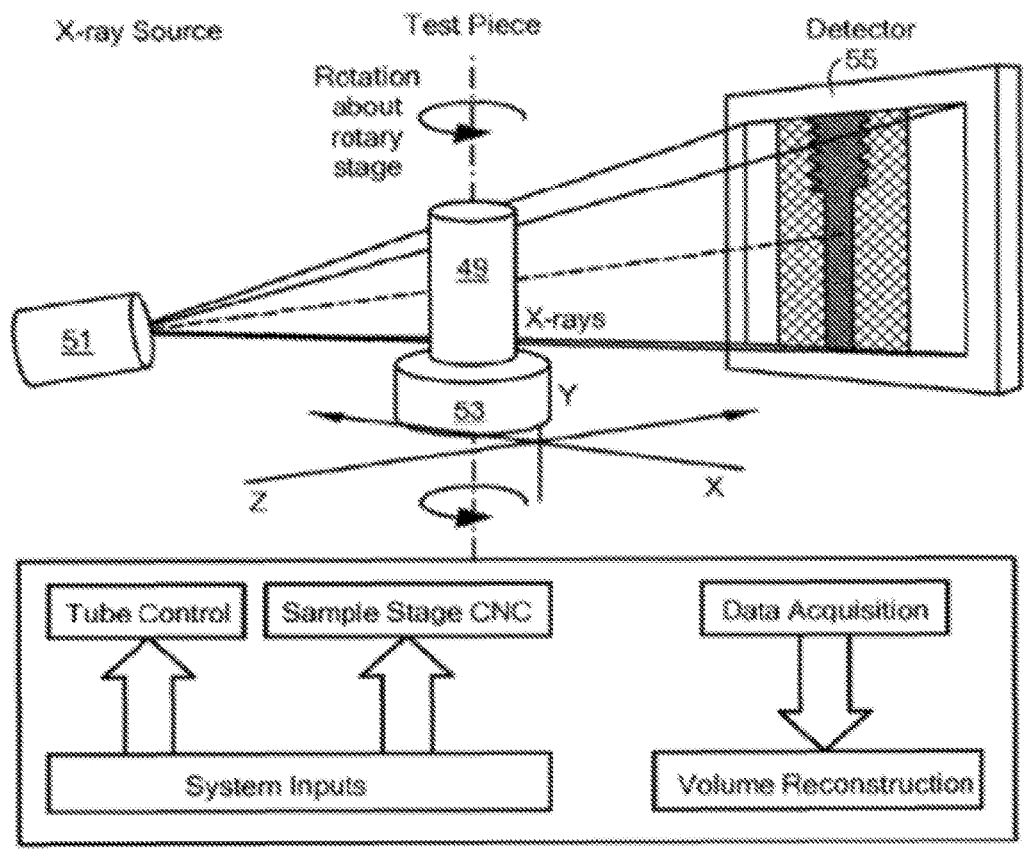
FIG. 1B schematically shows internal components of the device of FIG. 1A.

FIGS. 1A and 1B schematically show an x-ray machine/computed tomography device 10 that may use a calibration gauge configured in accordance with illustrative embodiments. It should be noted that although this discussion primarily relates to calibration, principles of various embodiments apply to verification of the accuracy of x-ray computed tomography machines 10. Accordingly, discussion of calibration is not intended to limit all embodiments of the invention.

Among other things, the x-ray CT machine 10 may be a computed tomography system (a/k/a a "CT system" or a "CT machine") that produces a three dimensional model of a work piece positioned within its interior (referred to as a "work piece reconstruction"). To those ends, the x-ray CT machine 10 has a housing 12 forming an interior chamber for containing, among other things (see FIG. 1B), 1) a work piece 49 to be measured, 2) an x-ray source 51 (also referred to as an "x-ray gun 51") for generating x-rays, 3) a rotary stage 53 for rotating the work piece 49, and 4) a detector 55 for detecting x-ray attenuation caused by the work piece after it is radiated by the x-ray gun 51. As known by those in the art, the detector 55 subsequently produces an x-ray image of the work piece. Returning to FIG. 1A, an access door 14, which may be formed from a transparent material, provides access to the interior for adding and removing work pieces 49. For example, the work piece 49 may be a cardiovascular stent commonly used in coronary angioplasty procedures. A control panel 16 on the side of the machine 10 acts as the control interface for an operator.

To produce the 3D model of the work piece 49 (the "reconstruction"), the CT system moves the work piece 49 relative to the x-ray guns 51. For example, the CT system may rotate the work piece 49 a full 360 degrees on the rotary stage 53, relative to the x-ray gun 52, to form the 3D reconstruction, and take multiple x-ray images (known in the art as "projections" or "projection angles" and noted above) of the work piece 49 during rotation. During and/or after rotating the work piece 49, a model building module (e.g., post-processing software executing on a local microprocessor or microcontroller) converts the data of all the projections into the noted 3D model of the work piece 49—the noted reconstruction. Stated another way, a 3D reconstruction typically is a 3D volume of a plurality of x-ray projections of the work piece 49. This data can be stored in memory, used to generate a point cloud, and/or used to measure the workpiece 49 (discussed below). Measuring the reconstruction generally produces more accurate measurements than other prior art techniques, such as measuring an x-ray projection on a display (e.g., measuring based on pixels). This is particularly apparent in the coordinate measurement machine (CMM) industry, where very small differences in accuracy (e.g., 1 millimeter or less) are significant. This is in contrast to many other applications, such as medical applications, that typically do not require such fine accuracy.

It is this 3D model—which may be a software model—that may be measured to confirm the dimensional accuracy of the work piece 49. Thus, even if the work piece 49 is a small medical device, such as a cardiovascular stent, then the measurement software may precisely measure selected features of the stent, such as its radius, wall thickness, etc.

If the CT system 10 is not properly calibrated, however, then these work piece measurements may be inaccurate. This is particularly problematic in metrology applications, which often require precise measurements. Accordingly, the operator or some other person should calibrate the CT system 10 prior to use. Such CT systems 10 used for precise measurement of workpieces 49 have verification standards, which define specifications and procedures for testing coordinate measuring machines with sensors relying on the principle of X-ray computed tomography. One such verification standard is provided by The Association of German Engineers ("VDI") and The Association for Electrical, Electronic & Information Technologies ("VDE") in VDI/VDE Directive 2630 Part 1.3, and titled "Computed tomography in dimensional measurement." Undesirably, however, the inventors know of no highly reliable and fine pitch technology, mechanism, or technique to conveniently verify the accuracy of conventional CT systems 10 to VDI/VDE verification standards at relatively steep angles. Recognizing that technical problem, the inventors have developed a highly accurate, fine pitch calibration/verification gauge that fills this deficiency in the art. Use of this gauge solves the problem that the prior technology known by the inventors lacks—the inability of such prior art technology of more efficiently calibrating and verifying such angles.

Figure 2A:
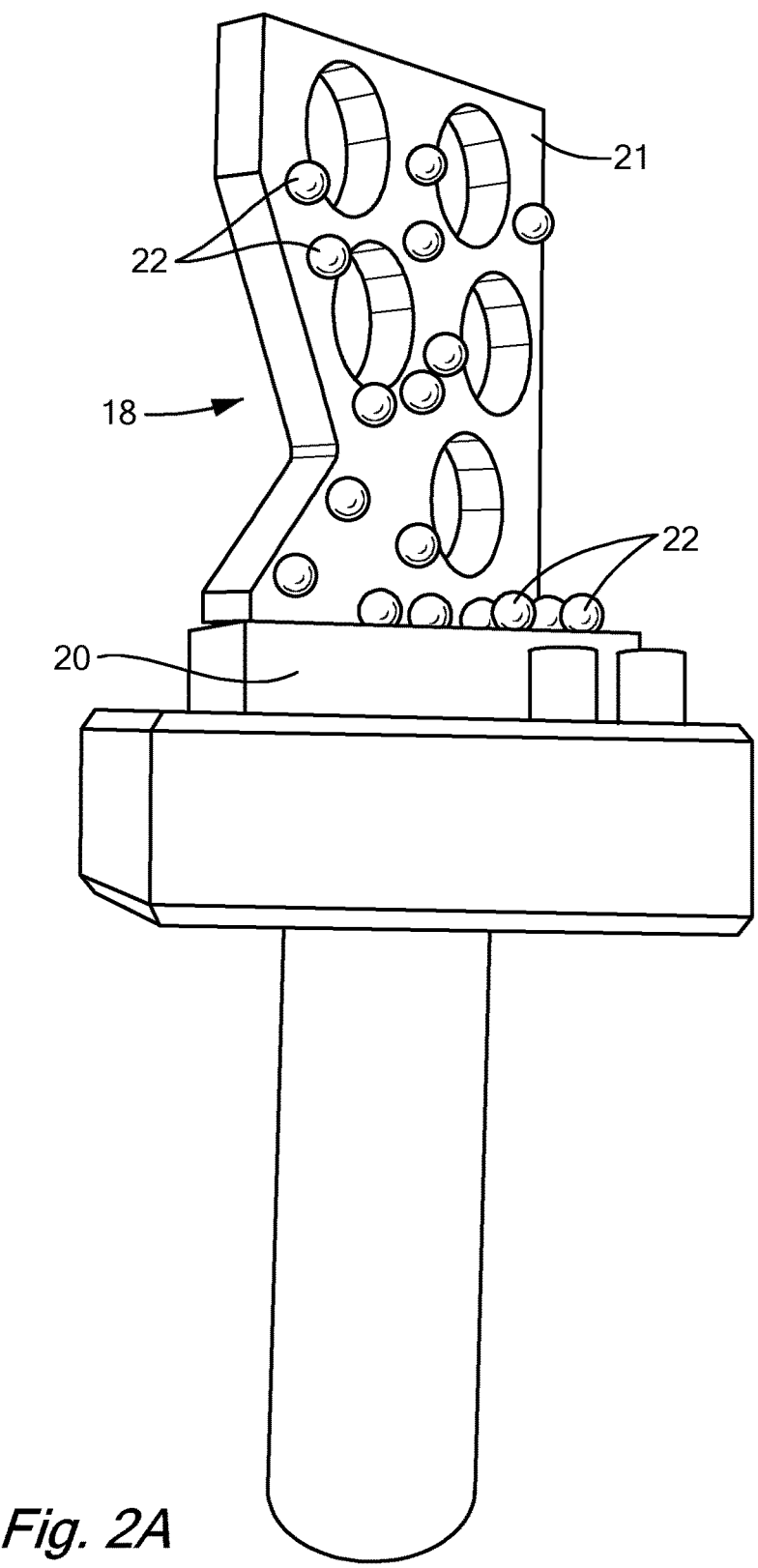
FIGS. 2A-2B schematically show an x-ray calibration and verification gauge configured in accordance with illustrative embodiments of the invention.
Figure 2B:
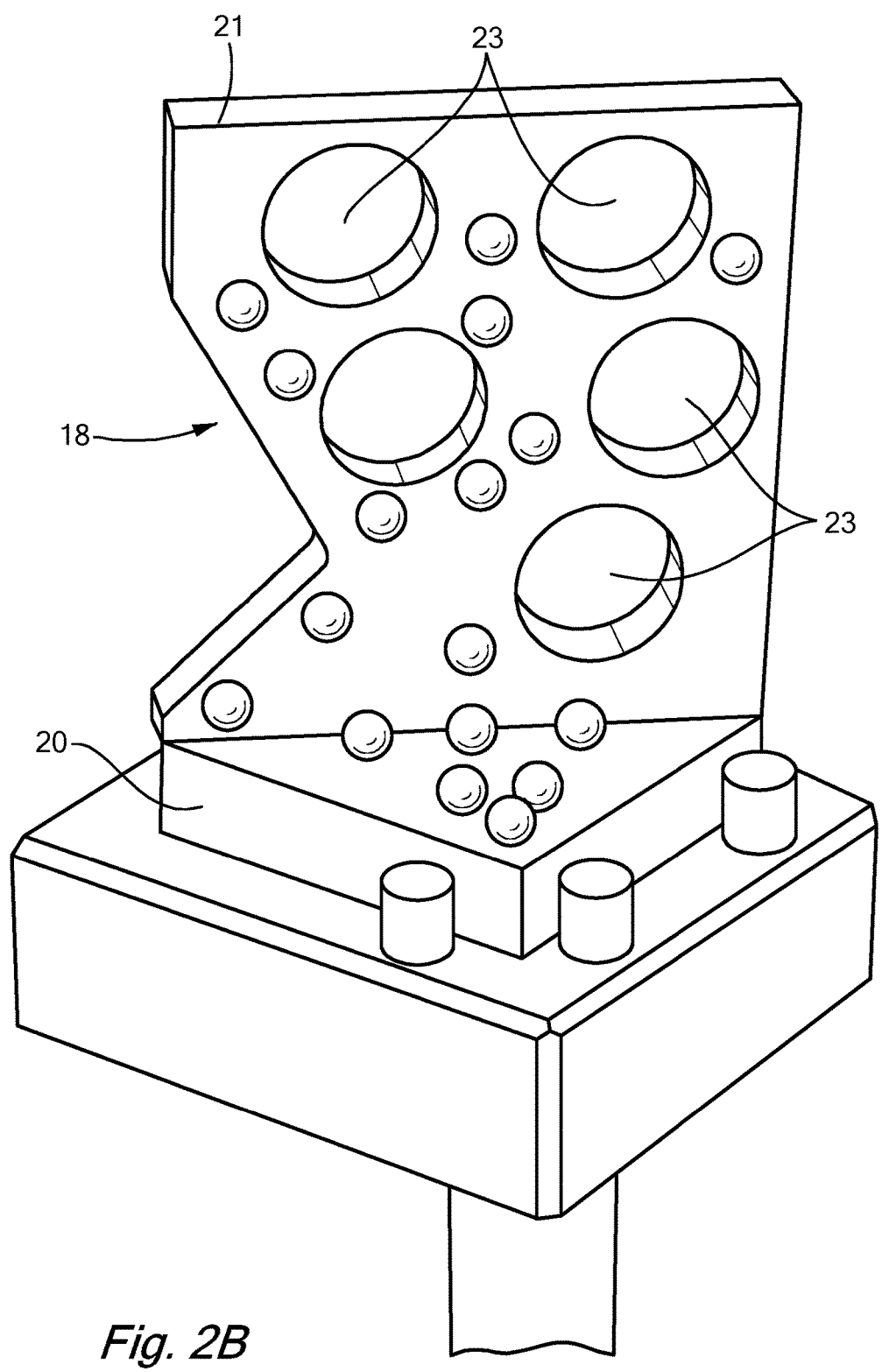

Specifically, FIGS. 2A-2B schematically show an illustrative gauge 18 for calibrating and/or verifying the CT machine 10. The gauge 18 has a first base 20 supporting a plurality of discrete objects 22 that act as guideposts in the calibration and/or verification process. More specifically, in illustrative embodiments, the objects 22 include three, four, or more spheres (also identified by reference number "22") that are ground or lapped to have very precise qualities (for example, precise symmetry, shape, size, volumes, centers, geometry, etc . . . ). In illustrative embodiments, the spheres 22 are certified by some reliable and well-known third party to have certain measurement qualities. In some embodiments, the spheres 22 are free-standing, immovable, and independent structures—they are not integral to or even connected to each other. Instead, spheres 22 merely contact the first base 20. In alternative embodiments, the spheres also may contact each other. As discussed in greater details below, some embodiments position the spheres 22 so that their centers form a measurement axis/straight line.

As noted above and discussed in greater detail below, the first base 20 couples the spheres 22 into place along predefined positions on the first base 20. The coupling may be accomplished by ultrasonic welding, adhesive and/or other techniques known to those skilled in the art. In particular, the spheres 22 are constrained so that they cannot move in any other manner, e.g., they cannot rotate or translate relative to the first base 20. Other embodiments, however, may permit non-translational motion, such as rotation relative to the first base 20.

The gauge 18 also has a second base 21 that supports a plurality of other, similar or identical discrete objects 22. In fact, the spheres 22 are coupled one or more surfaces of the second base 21. For example, spheres 22 may be coupled with both of the largest surfaces of the second base 21, and/or on one of the side surfaces. As shown in the figures, the first base 20 preferably is mounted to be substantially perpendicular to the second base 21. As shown, the first base 20 and the second base 21 form an open region free of objects 22—e.g., there are no other spheres 22 between the orthogonally mounted bases 20 and 21 (and no other bases 20 or 21). The first base 20 and second base 21 preferably are secured together in a "T" configuration (i.e., their combination generally resembles an upper case "T"). It should be understood that the term "substantially perpendicular" is intended to encompass various embodiments that are virtually perfectly perpendicular/orthogonal, as well as embodiments that are within an acceptably small tolerance of virtually perfectly perpendicular.

In a manner similar to the first base, 20, the second base 21 supports its spheres 22 in one or more parallel (or non-parallel) planes that are different than the one or more parallel (or non-parallel) planes of spheres 22 the first base 20 supports. While illustrative embodiments show the second base 21 as substantially perpendicular to the first base 20, this is not intended to limit all embodiments. Indeed, an acute, perpendicular or obtuse angle may be formed by the intersection of a longitudinal axis of the first base 20 with a longitudinal axis of the second base 21. Illustrative embodiments showing the second base 21 as planar and substantially perpendicular to the first base 20 are just exemplary and not intended to limit all embodiments. The second base 21 may be non-planar (not shown), and thus may support spheres 22 that lie on different tangential planes.

In illustrative embodiments, the second base 21 has x-ray attenuation features 23 (FIG. 2B). The features 23 are intended to minimize the amount of x-ray attenuation and photon deflection caused by the gauge 20 during scanning by the CT machine 10, while allowing the gauge 20 to maintain its structural integrity. More specifically, in illustrative embodiments, the features 23 comprise one or more holes (also identified by reference number "23") through the solid material forming the second base 21. These holes 23 may be precisely shaped and positioned to minimize interference with x-ray intensity. Optimization of the hole parameters refers to the maximum reduction of x-ray attenuation without significant effect on the structural integrity of the second base 21. To that end, structural analysis may be performed to optimize the hole characteristics (e.g., shape, size, etc.). Although shown as circular in the figures, the holes 23 can take on different shapes and sizes. The size and shape of the holes 23 depends on the material used to make the second base 21, as well as the number of spheres it will support.

Because a platform (e.g., the rotary table 53 of FIG. 1B) supports the first base 20, it can be formed from different materials, such as a less-rigid, less-x-ray attenuating material than that of the second base 21. To simplify production, however, illustrative embodiments of the gauge 18 form first base 20 and second base 21 from the same material. For example, the first and second bases 20 and 21 may be formed from boron nitride, and/or other materials having low coefficients of thermal expansion. A low coefficient of thermal expansion allows the geometric dimensions to remain relatively stable when temperature fluctuates. Some embodiments may have a structure similar to a truss that connects the spheres 22 along its joints.

The features 23 in the second base 21 are not limited to holes. A number of methods may be employed to reduce the amount of material that attenuates or deflects x-ray intensity. For example, portions of the second base 21 may be thinned, thereby reducing the amount of x-ray attenuation. Some embodiments may have recessed portions or grooves along the surface of the second base 21. In some embodiments, the spheres 22 may sit in the grooves. The second base 21 may have grooves with substantially straight and flat surfaces. For example, the surface of the groove may form a V-shape with an angle of between about 60 and 120 degrees. Additionally, or alternatively, the gauge 18 may also have protrusions on which the spheres 22 may be locked.

Furthermore, although FIGS. 2A-2B show the second base 21 positioned along the edge of the first base 20, other embodiments may position the bases 20 and 21 in a different manner relative to each other. Specifically, the second base 21 may attach to the first base 20 along any point, such as the middle of the top face of first base 20. Additionally, in some embodiments, the first base 20 does not necessarily attach/couple/fasten to the second base 21 at its bottom end. The first base 20 may attach to the second base 21 anywhere, including in the middle of the second base, again to form a "T" configuration (as noted above), or in a cross (e.g., "+") configuration. It should also be noted that not all embodiments require the first base 20 to be attached to the second base 21. In some embodiments, the bases may not be attached, and/or may not be in contact with one another.

To calibrate the CT system 10, a calibration module measures the distance between some identifiable regions of the various objects 22. For example, in the sphere 22 embodiment discussed above, the calibration module may measure between the centers of the one or more of the spheres 22. If the object 22 was not in the form of a sphere 22 (e.g., in the form of a protrusion, cube, cylinder, irregular shape, etc . . . ), then the identifiable region could be the center or some other area, such as an end, a discontinuity, a corner, the intersection of two portions, etc. Even if the objects 22 are spheres 22, the identifiable portion could be an outside region.

Accordingly, it is important for the spheres 22 to be visible on the x-ray images. To that end, the spheres 22 preferably are formed from a material having a higher attenuation to x-rays than that of the base 20. For example, the spheres 22 may be formed from aluminum oxide, such as ruby or sapphire, or other material with a low thermal expansion and x-ray attenuation near the middle of the range of intensity values of the CT system 10. As previously noted, the base(s) 20 and 21 may be formed from a ceramic material with a high stiffness and a low thermal expansion, but with an x-ray attenuation that is relatively low when compared to the material of the spheres 22. This differential in attenuations should be selected to provide good contrast and a clear separation between the surfaces of interest (i.e., the spheres 22) and the base(s) 20 and 21. For example, as noted above, the base(s) 20 and 21 preferably may be formed from boron nitride while the spheres preferably may be formed from ruby. Those in the art should understand that the base(s) 20 and 21 and spheres 22 may be formed from other materials having similar relative properties.

The coefficient of thermal expansions of the spheres 22, the first base 20, and the second base 21 preferably are as low as possible, such as no greater than that for steel. The first bases 20 and 21 also preferably are in a specified form to accurately support two or more spheres 22 in a precisely straight line. As noted herein, this line should be straight within a predefined error, such as 1 micron. This precision applies to spheres 22 that are on a single base 20 or 21, and also lines formed by spheres 22 on different bases 20 and 21 (e.g., one sphere on the first base 20 and another sphere on the second base 21).

To form a substantially straight line, the surfaces of the spheres 22 and the base 20 should be precisely configured. Specifically, as shown in FIGS. 4A and 4B (discussed in greater detail with regard to FIG. 3), the base 20 surface of this embodiment preferably is very planar, smooth, and straight. Ideally, each sphere 22 contacts the first base 20 at one infinitesimally small, discrete point. Of course, in illustrative embodiments, this contact is not infinitesimally small. The point of contact effectively forms a single force vector in a direction that is normal to the longitudinal axis of the first base 20.

Those skilled in the art should drive toward that end by using the more finely and accurately produced spheres 22. The spheres 22 thus may be formed to have a very fine precision. For example, the spheres 22 have a diameter with a precision to at least 0.01 millimeters. Specifically, as used herein, a precision of at least 0.01 millimeters may have an even finer precision, such as 0.001 millimeters, 0.005 millimeters, 0.0001 millimeter, 0.00001 millimeters, etc. As another example, the spheres 22 may have a diameter of 10.0001 millimeters, within some known tolerance, such as 0.00005 millimeters. All spheres 22 of the same gauge 18 may be the same size, or different. In either case, the diameters of the spheres 22 are known to the precision noted. Accordingly, illustrative embodiments can detect a variance of the reading by the CT machine 10 by an amount on the order of the precision of the sphere 22—down to the micrometer or nanometer level.

It should be noted that the above description regarding the first base 20 may apply to the second base 21, and vice-versa. For example, the first base 20 may have x-ray attenuation features, or be shaped to form a non-planar surface in a manner similar to the second base 21.

Figure 3:
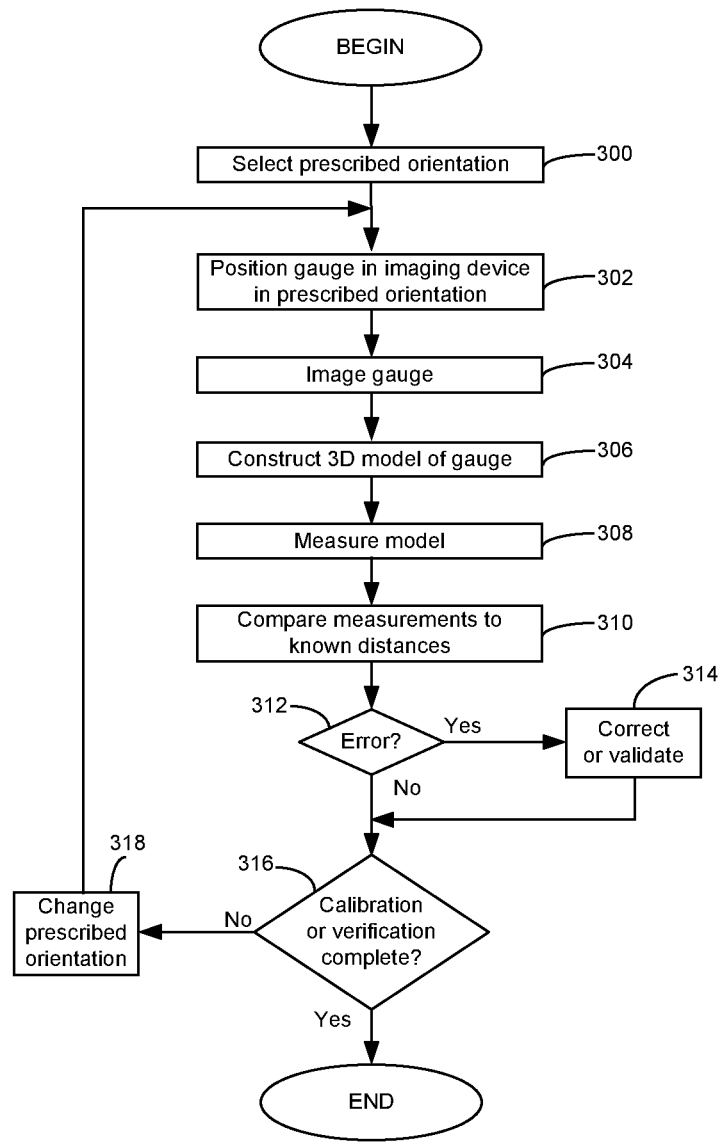
FIG. 3 shows a calibration and/or verification process using the gauge of FIGS. 2A-2B in the x-ray computed tomography device of FIG. 1 in accordance with illustrative embodiments of the invention.
Figure 4A:
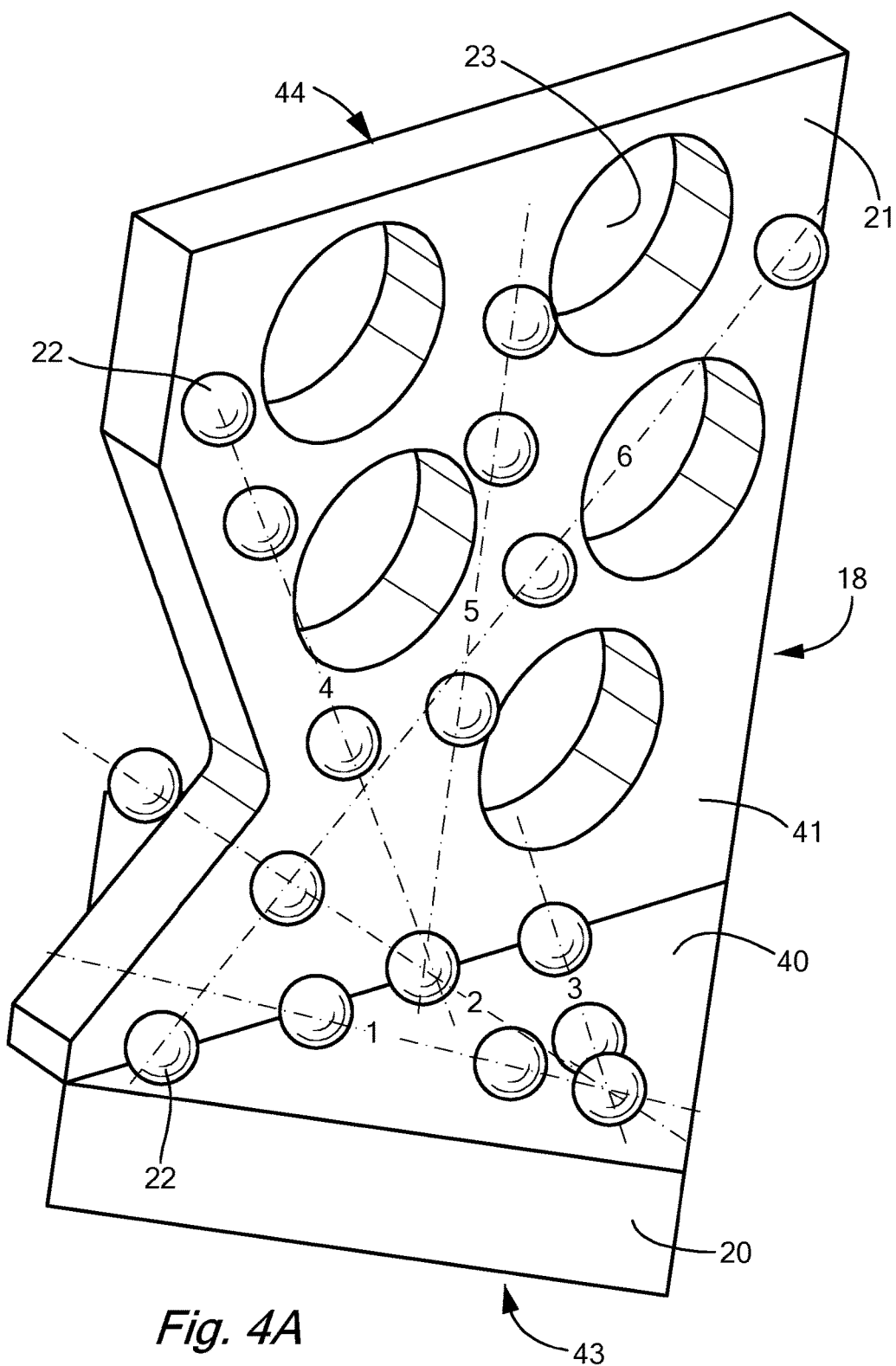
FIG. 4A schematically shows a perspective view of the gauge in accordance with illustrative embodiments of the invention.
Figure 4B:
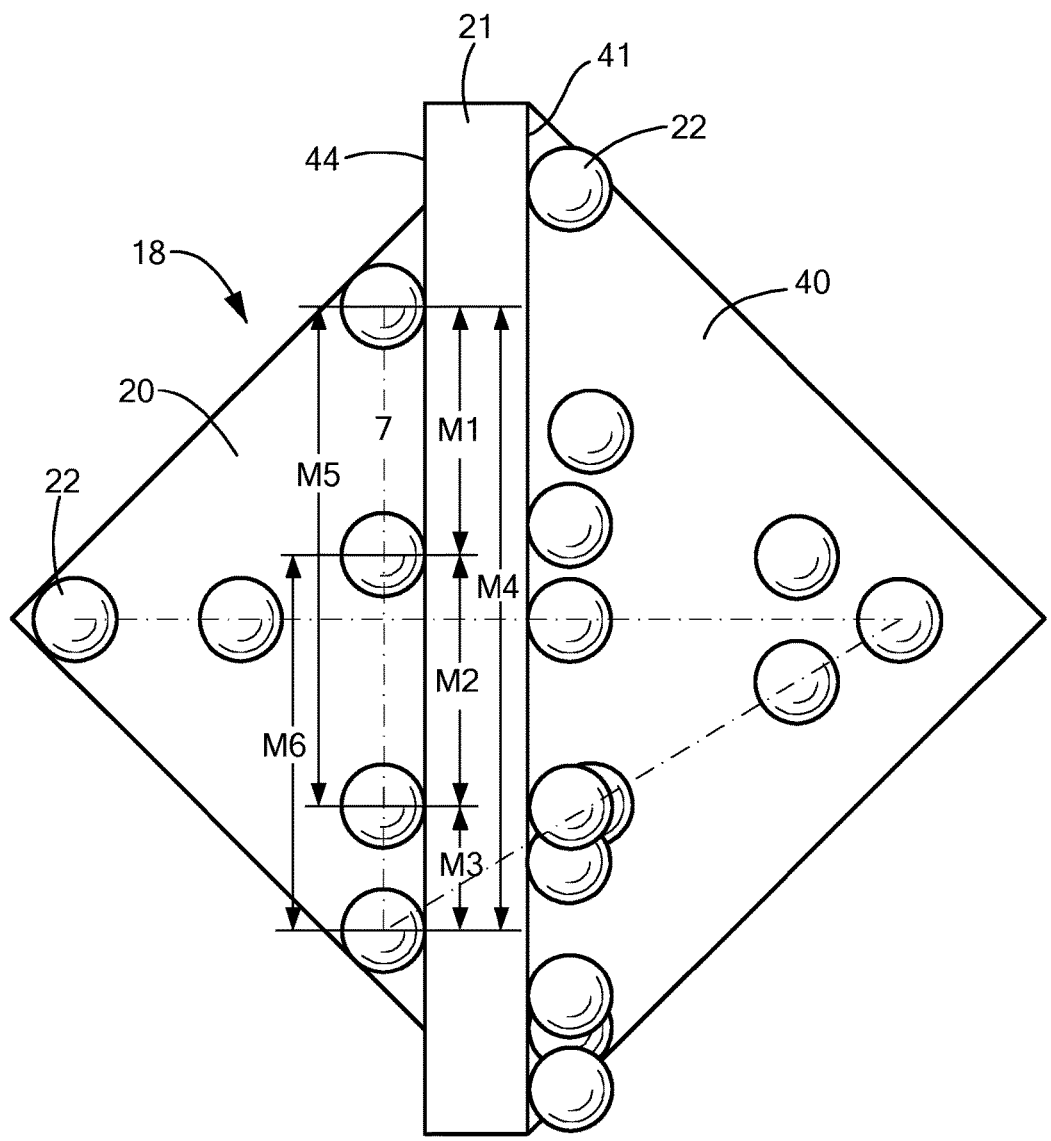
FIG. 4B schematically shows a top view of the gauge of FIG. 4A.

FIG. 3 shows a verification and/or calibration process that uses the gauge 18 in accordance with one embodiment of the invention. As noted above, this process provides a technical solution to a technical problem associated with prior art calibration and verification technology known by the inventor. Among other things, execution of this process ensures that the CT machine 10 is operating properly—a critical function for such a device. Catastrophic results can subsequently occur during use of a measured part if the CT machine is not operating properly—in this case, mis-measuring critical elements, such as stents or airplane propellers, could cause significant injuries.

It should be noted that this process is simplified from a longer verification and/or calibration process that may use the gauge 18. Accordingly, the process may have other steps that those skilled in the art may use. In addition, some of the steps may be performed in a different order than that shown, or at the same time. Those skilled in the art therefore can modify the process as appropriate.

The process begins at step 300 by selecting a prescribed orientation for the gauge 18 within the x-ray CT machine 10. For example, the first prescribed orientation may be relative to the X-axis of the CT machine 10. Next, the process physically positions the gauge 18 on the rotary stage 53 within the interior chamber of the CT machine 10 in the prescribed orientation (step 302). After the gauge 18 is positioned in the prescribed orientation within the interior chamber, the x-rays gun 51 and detector 55 cooperate to image the gauge 18 (step 304). To that end, the rotary table preferably rotates the gauge 18 a full 360 degrees. The axis of rotation in this example diverges (i.e., not parallel with) from at least one of the bases 20 and 21. In this example, the axis of rotation may be shown by line 5 of FIG. 4A, which is generally perpendicular to the first base 20. During this time, the x-ray gun 51 and detector 55 cooperate to generate a plurality of sequenced images/projections of the gauge 18 for subsequent processing. Each image may be stored in memory for subsequent reconstruction and processing.

After the CT machine 10 finishes imaging the gauge 18, the process constructs a three-dimensional model ("3D model") of the gauge 18 (step 306). A model engine (or model building module) thus uses the data from the successive images to construct the 3D model—a gauge 18 reconstruction, which also can be stored in memory. Although not necessary, rendering software may render the 3D model, and then rotate or otherwise move the ultimate 3D model in a viewer, thus showing the details of the gauge 18.

Step 308 then measures the 3D model elements (e.g., between reconstructed spheres 22) to determine if the CMM measurements are accurate—verifying accuracy. To that end, the process measures between preselected points within the gauge 18 reconstruction. For example, the process may measure from the center of each sphere 22 to the center of one or more of the other spheres 22. This step thus produces a plurality of values for verification in subsequent steps.

Some embodiments comply with VDI-VDE verification standards. Among other things, VDI-VDE verification standards specify that length measurement error tests compare known measurements with five measurements in each of seven different spatial directions. FIGS. 4A-4B schematically show an embodiment of the gauge 18 made to comply with such verification standards. Accordingly, the gauge 18 has a plurality of precisely positioned spheres 22 that permit five measurements in each of seven different spatial directions. As with other gauge embodiments, the first base 20 and the second base 21 are configured substantially perpendicularly to each other. This substantially perpendicular configuration provides a wider variety of potential measurements than that of a 2D standard gauge. Specifically, measurements may be taken in three dimensions, at steep angles, and at a fine pitch.

FIG. 4A shows examples of six different spatial directions 1-6 for measuring 3D model elements (e.g., spheres 22). The top view of FIG. 4B shows a seventh example spatial direction 7. Each of those directions effectively forms a straight line or vector. Each straight line in this embodiment has four or more spheres 22, although other embodiments may have fewer spheres 22. The spheres in a given line may be positioned on opposite sides of the second base 21, across the first base 20.

These spatial directions/lines are merely exemplary and not intended to limit embodiments of the invention. As shown, various embodiments are not limited to directions along each of the orthogonal planes. Measurements may be taken in spatial directions that traverse both planes formed, for example, by a top surface 40 of the first base 20 and a front surface 41 of the second base 21. For example, placing two spheres 22 on the top surface 40 of the first base 20 and two spheres 22 on the front surface 41 and rear surface 44 of the second base 21 may create a spatial direction if the four spheres 22 are aligned. One of those spheres 22 may be coupled/supported/contacting both the first and second bases 20 and 21. Such a sphere 22 thus can be shared by different lines, minimizing the required number of spheres 22 in the gauge. For example, lines 2 and 5 share a sphere 22 that contacts both bases 20 and 21. A person having skill in the art should know how to position spheres 22 on the gauge 18 to create multiple spatial directions. Some embodiments may place spheres 22 within the holes 23 to provide another measurement point.

It should be noted that some of the lines 1-7 may appear in the figures to contact spheres 22 that would make the lines not straight. For example, line 2 does not pass through the sphere spaced away from the top surface 40 of the first base 20. Such a suggestion is merely a limitation of a 2-D drawing.

The substantially perpendicular configuration of the first base 20 and the second base 21 enables fine pitch measurements in three dimensions. For example, a line (also referred to as a "measurement axis") may be formed by a sphere 22 positioned near the top of the second base 21, and a first base sphere 22 slightly offset from the intersection of the bases 20 and 21. Additionally, more spheres 22 may lie within that axis. Some embodiments of the first base 20 and/or the second base 21 have protrusions on which some of the spheres 22 rest to facilitate fine pitch measurements.

While a spatial direction may be formed between two spheres 22, preferred embodiments use at least four axially aligned spheres 22 to form a single spatial direction/measurement axis. FIG. 4B shows an example of such a measurement axis—line 7. Four first base spheres 22 aligned in a single spatial direction 7 enable six different measurements (M1-M6) in the spatial direction 7. Specifically, measurements may be taken between the center of each adjacent sphere (M1-M3), between the centers of the first sphere 22 and the fourth sphere 22 (M4), between the centers of the first sphere 22 and the third sphere 22 (M5), and between the centers of the second sphere 22 and the fourth sphere 22 (M6). The method may use any five of these measurements, or all six of the measurements.

The actual distance between the prespecified points is known; in preferred embodiments, those distances are certified. For example, the known distance between the centers of two spheres 22 can be 10.0001 millimeters. The known distance between the centers of two other spheres 22 could be 20.0002 millimeters. Other embodiments can vary the distance between the different spheres 22.

Step 310 compares those different measured distances against the known distances and determines if there are discrepancies, which indicates errors (step 312). For example, the process simply may use logic to determine the difference between the various measurements and the known distances. This difference is the calibration error of the machine 10. Using the example above, if the measured distance between the first two spheres 22 (known distance 10.0001 millimeters) is 10.0004 millimeters, then the CT machine 10 has an error of 0.0003 millimeters and thus, should be appropriated adjusted/re-calibrated. Illustrative embodiments complying with the VDI-VDE standard compare the calibration error in five measured distances in each of seven spatial directions (35 total measurements).

Accordingly, if the process detects errors beyond some preset limits or tolerances (e.g., detecting this exemplary 0.0003 millimeter error) and the process is a calibration process, then step 314 corrects the error by refining the initial calibration settings of the CT system 10. Of course, if errors are not beyond the noted preset limits, then the process does not adjust the calibration settings. After correcting the errors by step 314, or if there are no errors from step 312, the process continues to step 316 to determine if calibration or verification is complete. If it is complete, then the process ends. If not complete, then the process may change the prescribed orientation of the gauge 18. For example, the prescribed orientation can be moved to be orthogonal to the initial prescribed orientation. By doing this, the operator can test various different axes within the machine.

Some embodiments may skip 314. Instead, such embodiments may execute step 314 after the CT machine 10 images all orientations of the gauge 18.

Potential applications of various embodiments may include (in addition to those noted above or reiterating those above):

CT CMM verification and validation, and acceptance testing,

Using the spheres 22 on a horizontally oriented base 20 or 21 for in-plane CT performances evaluation—hardware and imaging algorithms.

Using the spheres 22 on a vertically oriented base 20 or 21 for cone beam evaluation—hardware and imaging algorithms.

Multiple repeated distances in each orientation, which can be used for comparing CT reconstruction performances along each orientation.

With reference to coordinate measuring machine measurements, gauge measurements can be used for developing and improving hardware and imaging algorithms, including calibrations and corrections.

Use of the gauge 18 in a wide variety of CT systems, such as industrial CT, microCT, medical CT, etc.

Similar to its CT applications, the gauge 18 also can be used for 2D X-ray systems for development, verification and validation.

Accordingly, using the reconstruction to measure prescribed distances provides precise measurements to verify or calibrate the CT system 10. This is especially important in metrology applications, which, as noted above, often require highly precise and fine measurements. The inventor expects such a method to be superior to simply measuring x-ray projections on a pixelated display device, which can have an error that is unacceptable in many metrology applications. Moreover, use of three or four objects 22 in a single line, and sharing objects 22 between the two bases 20 and 21 similarly enhances gauge efficiency (e.g., gauge manufacture, and reduced set-up for comprehensive characterization of system accuracy).

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the flow chart described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A method of calibrating or verifying the dimensional accuracy of an x-ray computed tomography machine, the method comprising:
   controlling the x-ray computed tomography machine to image a gauge to produce a 3D gauge reconstruction with reconstructed features of the gauge, the gauge comprising a plurality of objects formed from an object material, a first base supporting two or more of the objects, and a second base supporting another two or more of the objects, the first and second bases formed from a base material, the object material having a higher x-ray attenuation value than the base material, the first base forming a first plane, the second base forming a second plane, the first plane and the second plane being substantially perpendicular to each other, each of the objects being secured on at least one of the first base and the second base, each of the objects having a center, the distance between the centers of each object being known center distance values;
   measuring, in the 3D gauge reconstruction, the distance between at least two objects to produce measured center distance values;
   comparing the measured center distance values against the known center distance values; and
   using the comparison to determine if there is a distance error in the x-ray computed tomography machine.

2. The method as defined by claim 1 wherein at least one of the first base and the second base has at least one hole through solid base material.

3. The method as defined by claim 1 wherein the second base contacts the first base along an edge of the first base.

4. The method as defined by claim 1 wherein each of the objects is substantially spherically shaped and identically sized.

5. The method as defined by claim 1 wherein each of the objects comprises ruby material.

6. The method as defined by claim 1 wherein at least one of the objects contacts both the first base and the second base.

7. The method as defined by claim 1 wherein first, second, and third objects of the plurality of objects form a substantially straight line, further wherein measuring comprises measuring between the first and second objects, and measuring between the first and third objects.

8. The method as defined by claim 7 wherein a fourth object of the plurality of objects is part of the substantially straight line, further wherein measuring comprises measuring between the fourth object and at least one of the first, second and third objects.

9. The method as defined by claim 1 wherein controlling the x-ray comprises:
   producing a plurality of 3D gauge reconstructions of the gauge from a plurality of x-ray projection images in different orientations, the method further comparing the measured center distance values of the objects in each of the 3D gauge reconstructions against the respective known center distance values.

10. The method as defined by claim 1 further comprising:
    determining that there is no distance error; and
    maintaining the calibration settings in the x-ray computed tomography machine in response to determining that there is not a distance error.

11. The method as defined by claim 1 further comprising:
    determining that there is a distance error; and
    modifying the calibration settings of the x-ray computed tomography machine in response to determining that there is a distance error.

12. The method as defined by claim 11 further comprising:
    determining the difference between the measured center distance values and the known center distance values, modifying the calibration settings being a function of at least one of the differences.

13. The method as defined by claim 1 wherein the objects include a given type of object, the first base and the second base each supporting at least two of the given type of object.

14. The method as defined by claim 1 wherein controlling comprises controlling the x-ray computed topography machine to scan around the gauge about an axis of rotation that diverges with either a) the first plane, b) the second plane, or c) both the first plane and the second plane.

15. The method as defined by claim 1 wherein the 3D gauge reconstruction comprises a point cloud.

16. A computer program product for use on a computer system for calibrating or verifying the dimensional accuracy of an x-ray computed tomography machine, the computer program product comprising a tangible, non-transient computer usable medium having computer readable program code thereon, the computer readable program code comprising:

program code for controlling the x-ray computed tomography machine to image a gauge to produce a 3D gauge reconstruction with reconstructed features of the gauge, the gauge comprising a plurality of objects formed from an object material, a first base supporting two or more of the objects, and a second base supporting another two or more of the objects, the first and second bases formed from a base material, the object material having a higher x-ray attenuation value than the base material, the first base forming a first plane, the second base forming a second plane, the first plane and second plane being substantially perpendicular to each other, each of the objects being secured on at least one of the first base and the second base, each of the objects having a center, the distance between the centers of each object being known center distance values;

program code for measuring, in the 3D gauge reconstruction, the distance between at least two objects to produce measured center distance values;

program code for comparing the measured center distance values against the known center distance values; and program code for using the comparison to determine if there is a distance error in the x-ray computed tomography machine.

17. The computer program product as defined by claim 16 wherein the program code for controlling comprises program code for controlling the x-ray computed topography machine to scan around the gauge about an axis of rotation that diverges with either a) the first plane, b) the second plane, or c) both the first plane and the second plane.

18. The computer program product as defined by claim 16 wherein first, second, and third objects of the plurality of objects form a substantially straight line, further wherein the program code for measuring comprises program code for measuring between the first and second objects, and program code for measuring between the first and third objects.

19. The computer program product as defined by claim 18 wherein a fourth object of the plurality of objects is part of the substantially straight line, further wherein program code for measuring comprises program code for measuring between the fourth object and at least one of the first, second and third objects.

20. A gauge for calibrating or verifying the dimensional accuracy of an x-ray computed tomography machine, the gauge comprising:

a plurality of objects formed from a material that is visible to x-rays, the plurality of objects being configured to receive x-rays without changing shape, each of the plurality of objects having substantially the same shape, the objects each having an object attenuation value to x-rays;

a substantially planar first base fixedly supporting a first set of the plurality of objects;

a substantially planar second base fixedly supporting a second set of the plurality objects, the first and second sets of objects having a common object, the first base having a first base attenuation value, the second base having a second base attenuation value, the object attenuation value being greater than the first and second base attenuation values, the first base being connected to the second base.

21. The gauge as defined by claim 20 wherein the first and second sets of the plurality of objects includes a first object, a second object, a third object and a fourth object that together align to form a substantially straight line.

22. The gauge as defined by claim 21 wherein at least one of the first, second, third and fourth objects are in both the first and second sets of the plurality of objects.

23. The gauge as defined by claim 20 wherein at least one of the first base and the second base comprises a solid base material forming at least one hole through solid base material.

24. The gauge as defined by claim 20 wherein the second base contacts the first base along an edge of the first base to form a "T" shape.

25. The gauge as defined by claim 20 wherein the first base and the second base form an open region free of objects.

26. The gauge as defined by claim 20 wherein the first base forms a right angle with the second base.

27. The gauge as defined by claim 1 wherein the first base has at least three collinear spheres mounted thereon, and the second base has at least three collinear spheres mounted thereon.

28. The gauge as defined by claim 1 wherein the first base has three non-collinear spheres mounted thereon that define a plane that is parallel to the first base, and the second base has three non-collinear spheres mounted thereon that define a plane that is perpendicular to the first base.

\* \* \* \* \*